United States Patent
Azure

[19]

[11] Patent Number: 5,908,444
[45] Date of Patent: Jun. 1, 1999

[54] COMPLEX FREQUENCY PULSED ELECTROMAGNETIC GENERATOR AND METHOD OF USE

[75] Inventor: Larry Azure, LaConner, Wash.

[73] Assignee: Healing Machines, Inc., LaConner, Wash.

[21] Appl. No.: 08/878,996

[22] Filed: Jun. 19, 1997

[51] Int. Cl.⁶ .................................................... A61N 5/00
[52] U.S. Cl. .................................. 607/88; 607/1; 607/69; 600/14
[58] Field of Search ................................ 600/10, 11, 13, 600/14, 26, 27; 607/88, 90, 1, 103, 69–71; 361/230, 232, 229; 313/153, 154

[56] References Cited

U.S. PATENT DOCUMENTS

| | | | |
|---|---|---|---|
| 3,773,049 | 11/1973 | Rabichev et al. ........................... | 607/1 |
| 3,785,383 | 1/1974 | Dotto ........................................ | 607/90 |
| 4,793,325 | 12/1988 | Cadossi et al. ........................... | 600/14 |
| 4,909,255 | 3/1990 | Farin ....................................... | 128/420 |
| 4,911,686 | 3/1990 | Thaler ...................................... | 600/14 |
| 5,197,940 | 3/1993 | Sievert et al. ........................... | 607/103 |
| 5,453,072 | 9/1995 | Anninos et al. ........................... | 600/9 |
| 5,556,418 | 9/1996 | Pappas ..................................... | 607/1 |
| 5,743,844 | 4/1998 | Tepper et al. ............................ | 600/14 |

*Primary Examiner*—Beverly M. Flanagan
*Assistant Examiner*—Bryan K. Yarnell
*Attorney, Agent, or Firm*—Seed and Berry LLP

[57] ABSTRACT

A pulsing electromagnetic field is generated by a tuned Tesla coil, and a plurality of pulsed signals having selected frequencies synchronously with the pulsing magnetic field. A patient is placed proximate to the Tesla coil to receive the pulsing electromagnetic field and the pulsed signals. A second pulsing magnetic field is generated to be applied to a selected portion of the patient. Methods for treating patients afflicted with a variety of conditions is also disclosed.

17 Claims, 3 Drawing Sheets

COMPLEX FREQUENCY PULSED ELECTROMAGNETIC GENERATOR AND METHOD OF USE

TECHNICAL FIELD

This invention relates to pulsed electromagnetic fields, and more particularly, to a system and method for the treatment of various diseases, including AIDS-related illnesses using complex frequency pulsed electromagnetic fields.

BACKGROUND OF THE INVENTION

Individual cells in a patient are electrochemical units having a metabolic chemistry with both electrical and chemical properties. Each cell is surrounded by a membrane which acts a "battery" that is continually recharged by the metabolic chemistry of the cell. The cell supports an electrical potential across the membrane, called a transmembrane potential (TMP), which varies in a healthy cell from about 70 to 100 millivolts.

When the energy level (bioenergy) of a "sick" cell is reduced by trauma, disease, parasitic infection such as HIV or malnutrition, the TMP falls along with the biochemical metabolism, especially production of adenosine triphosphate (ATP), until the cell either recovers, undergoes mitosis or dies.

Harmless irradiation of the body by exogenic, non-ionizing pulsed electromagnetic fields (PEMFs) for short periods (i.e., minutes) at long intervals (i.e., days or weeks) has been shown to be highly effective in relieving pain, healing trauma and clearing or controlling infections.

The healing of diseased or damaged cells is enhanced by the application of electrical current directly to an area of the body, or by exposing an area of the body to an electromagnetic field to induce an electrical current in the diseased or damaged cells. The added current aids healing by raising the TMP and restoring energy to the cells. The electrical current supports the exchange of potassium and sodium ions, and facilitates the production of adenosine triphosphate (ATP). Normal healthy cells are not adversely affected by the added current because a membrane with a normal TMP will not accept additional charge.

Electromagnetic fields have been applied to treat a number of diseases. For example, cancer cells have been exposed to electromagnetic fields. It is believed that, as a typical cancer cell grows, its TMP falls. The growing cancer cell will undergo mitosis when its TMP falls below a threshold. The application of an electromagnetic field can maintain the TMP of a cancer cell above the threshold to prevent the mitosis from occurring. As a result, the cancer cell grows too large for its membrane and cannot absorb sufficient nutrients to survive. Eventually, the cancer cell dies. Electromagnetic fields have also been applied to treat bacterial infections, relieve pain, and to eliminate tapeworm and hookworm infestations.

The reaction of various species of sick cells is frequency dependent. However, the frequencies required by specific cells is not readily determined. Accordingly, there is a need in the art for a system and method for treating individuals with complex frequency PEMFs. The present invention provides this, and other advantages as will be apparent from the following figures and accompanying detailed description.

SUMMARY OF THE INVENTION

In one embodiment, the present invention is directed to an apparatus for generating pulsed electromagnetic fields. The apparatus includes a signal generator circuit generating first voltage pulses. A resonant circuit having a first coil is coupled to the pulse generator circuit and receives the first voltage pulses. The resonant circuit generates a first pulsing electromagnetic field in response to the first voltage pulses. The apparatus also includes a second coil coupled to the pulse generator circuit to receive the first voltage pulses. The second coil generates a second pulsing electromagnetic field in response to the first voltage pulses. The first and second pulsing electromagnetic fields are time-synchronized with each other by the first voltage pulses.

The pulse generator circuit may comprise a plasma discharge circuit. Alternatively, the pulse generator may comprise first and second electrodes spaced apart from each other at a variable distance and generating a short duration plasma discharge between the first and second electrodes at a predetermined time interval. In an exemplary embodiment, the pulse generator generates the first voltage pulses at variable time intervals. Alternatively, the pulses may be generated at a predetermined fixed time interval. The pulse generator is inductively coupled to the resonant circuit by a third coil. The first pulsing electromagnetic field encompasses frequencies in the radio frequency spectrum.

The system may also include a light emitting system including at least a first translucent gas-filled tube. The light emitting system emits an electromagnetic signal having one or more selected frequencies in response to the first pulsing electromagnetic field. The light emitting system may include a plurality of translucent gas-filled tubes, each containing a selected gas to emit light at a wavelength corresponding to the selected gas.

The apparatus of this invention may be used for the therapeutic treatment of a patient wherein the patient is positioned in proximity with the resonant circuit so as to be generally subjected to the first pulsing electromagnetic field throughout the whole body. The second coil is positionable in proximity with a selected portion of the patient to subject the selected portion of the patient's body to the second pulsing electromagnetic signal.

In another embodiment, a method is disclosed for treating AIDS in a patient in need thereof by use of a bio-electric light simulating unit. In the inventive method, the patient is seated in proximity with a bio-electric stimulator unit and generally exposed to pulsing electromagnetic fields. The method may also include the generation of electromagnetic signals having wavelengths in the visible light region. The patient is exposed generally to the pulsing electromagnetic field and the pulsing light emissions for a period of time necessary to treat the individual patient.

DETAILED DESCRIPTION OF THE INVENTION

Electromagnetic fields are increasingly being used to treat diseases in both human and animal patients. Individual cells in a patient function in an electrical environment which influences the health of the cells. The electrical environment of the cells may be modified by placing the patient in the proximity of an electromagnetic (EM) field. It is believed that the presence of an EM field has a beneficial impact on diseased or damaged cells and, therefore, a need exists for a device to generate an appropriate EM field and a method for treating patients with the EM field generated by the device.

Because the reaction of various types of cells is frequency dependent, the present invention advantageously provides a wide spectrum of harmonics up to approximately 2 GHz. In addition, the present invention provides selected wavelengths within the visible spectrum. Although not intended to be limited by the following theory, the physiological basis for the effectiveness of the present invention is believed to be as follows: at a cellular level, magnetic fields penetrating the body generate microcurrents that are incrementally rectified by the non-linear impedance of cell membranes in such a manner as to increase TMP, and consequently ATP production, in effect heightening the cell's bioenergy.

At a molecular level, the alternating electrical field (1) at some specific frequency within the pulse spectrum may excite specific molecular resonance such as to accelerate biochemical processes, and/or (2) the bipolar oscillations of the electric fields may excite mechanical vibrations of electrically charged molecules (anions/cations) in the tissues to produce acoustic energy that operates to increase blood flow and membrane permeability (electroporosis). At an atomic level, the alternating magnetic fields may affect electron spin and/or linkage bonds in such a manner as to expedite biochemical processes.

Figure 1:
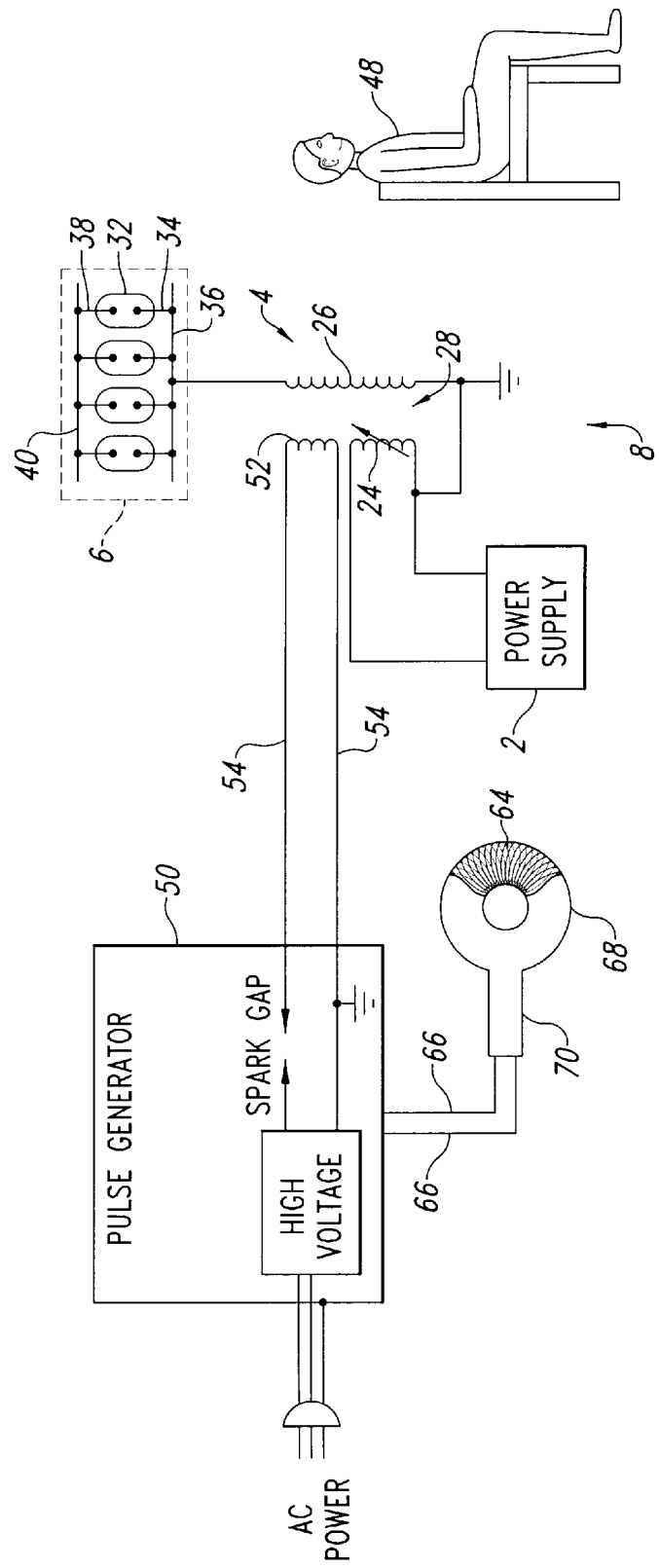
FIG. 1 is a schematic diagram of an apparatus for generating several electromagnetic fields according to an embodiment of the invention.

An apparatus for generating PEMFs according to an embodiment of the invention is shown in FIG. 1. The present invention is embodied in a system 49 illustrated in FIG. 1. The system 49 includes a power supply 2, which supplies high voltages to an air core resonant transformer 4, which in turn generates a resonant electric field. The resonant electric field induces electromagnetic radiation from the air core resonant transformer 4 and a light emitting system 6. The power supply 2, air core resonant transformer 4 and light emitting system 6 are available as a commercial product, known as a bio-electric light stimulator unit (BELS unit) 8. Operational details of the BELS unit 8 are provided below.

Figure 2:
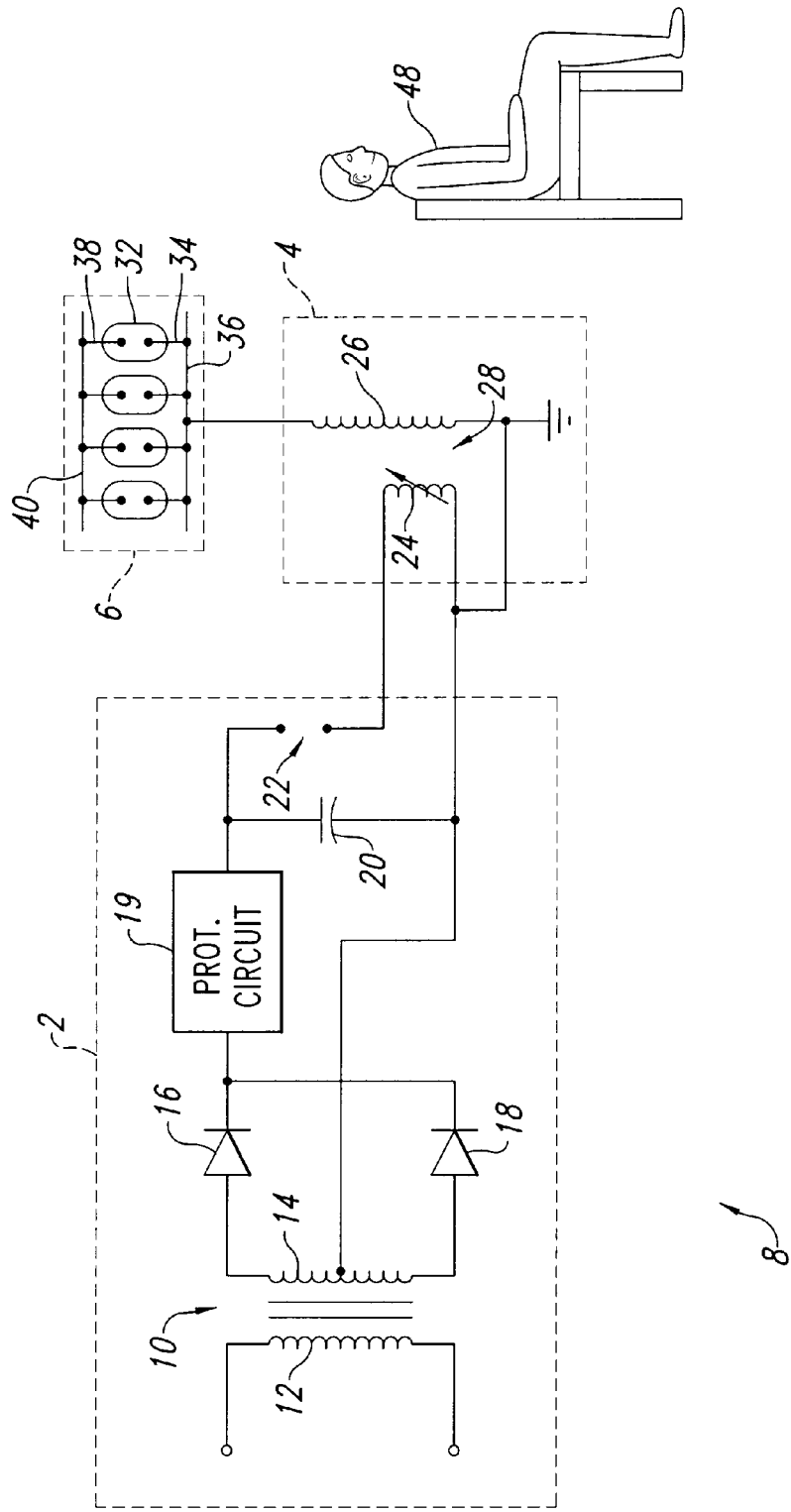
FIG. 2 is a schematic diagram of a bio-electrical light stimulator unit used in a treatment method of the present invention.

As illustrated in FIG. 2, the power supply 2 includes a transformer 10 having a primary winding 12 coupled through a magnetic core to a secondary winding 14. The secondary winding 14 is tapped at a midpoint to a ground. The secondary winding 14 is connected between the anodes of two diodes 16 and 18 forming a fullwave rectifier. A protection circuit 19 protects the diodes 16 and 18 and the transformer 12 from high voltages generated by the other portions of the BELS unit. The protection circuit 19 may be an RF choke, additional diodes with a high peak inverse voltage rating, or the like. The cathodes of the diodes 16 and 18 are both connected to a first plate of a capacitor 20 and to a first terminal of a spark gap 22. A second plate of the capacitor 20 is connected to the ground.

The air core resonant transformer 4 is coupled to the power supply 2 through a second terminal of the spark gap 22, which is connected to a first end of a variable inductor 24. A second end of the variable inductor 24 is connected to the ground. The variable inductor 24 is coupled to a Tesla coil 26 across an air gap 28. The air gap 28 is made as small as possible to minimize losses in the coupling. However, the air gap 28 must be large enough to prevent arcing between the variable inductor 24 and the Tesla coil 26. A first end of the Tesla coil 26 is connected to the light emitting system 6 and a second end of the Tesla coil 26 is connected to the ground.

The light emitting system 6 may be constructed of one or more translucent tubes 32, each tube enclosing a selected gas in the following manner. A first electrode 34 extends from an interior volume of the tube 32 through a first end and is connected to a first plate 36. A second electrode 38 extends from the interior volume of the tube 32 through a second end and is connected to a second plate 40. The first plate 36 is connected to the first end of a Tesla coil 26. Each of the tubes 32 in the light emitting system 6 may contain one or more of the following gases: hydrogen, helium, argon, neon, xenon, Krypton, water vapor, oxygen, or nitrogen. Each of the listed gases emits electromagnetic waves over a range of frequencies, including frequencies in the visible portion of the electromagnetic spectrum, when the gas is ionized by a substantial electric field. Of course, other gases may also be used to provide electromagnetic waves of different frequencies.

The operation of the BELS unit 8 itself may now be described. A standard 120 V, 60 Hz AC line signal is applied to the primary coil 12 of the transformer 10, and a 6,000 V AC signal is generated by the transformer 10 in the secondary coil 14. The signal in the secondary coil 14 is rectified by the diodes 16 and 18 and the rectified signal is applied to the first plate of the capacitor 20. When the first plate of the capacitor 20 is charged to a threshold voltage which exceeds the breakdown voltage of the spark gap 22, there is a discharge of a voltage pulse in the form of an arc or a spark across the spark gap 22. The voltage pulse is drawn through the variable inductor 24 to the ground. After the discharge of the voltage pulse across the spark gap 22, the first plate of the capacitor 20 continues to be charged by the rectified voltage until the threshold voltage is reached, at which point another voltage pulse is driven through the variable inductor.

Figure 3:
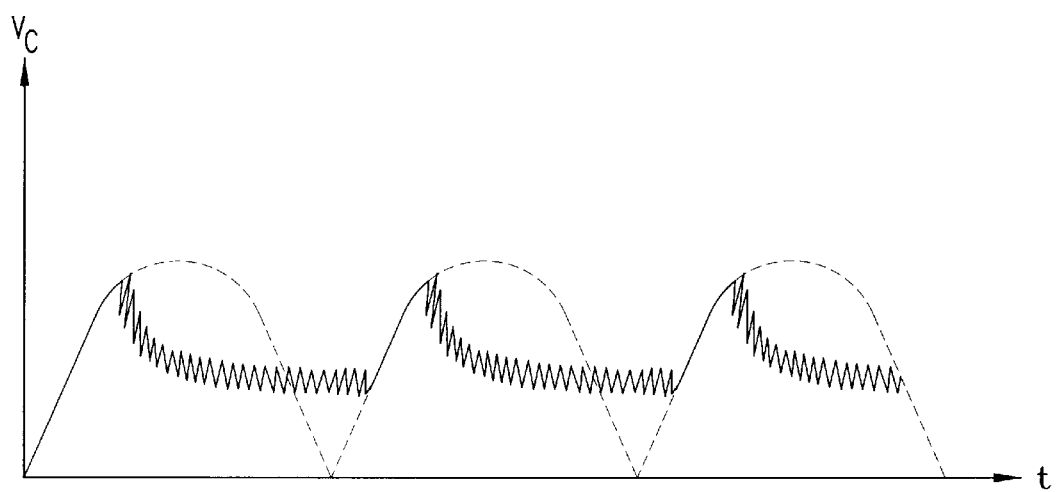
FIG. 3 is a waveform automatically generated by the system of FIG. 2.

A plot of a voltage Vc on the first plate of the capacitor 20 is shown in FIG. 3. The capacitor 20 is charged by a 120 Hz signal and discharges every cycle at the threshold voltage. The discharge results in noise which is reflected in the voltage Vc as it falls during a discharge. The voltage Vc begins to rise in the next cycle of the rectified signal.

The threshold voltage may be adjusted by changing the distance between the first and second terminals of the spark gap 22. If the distance between the terminals of the spark gap 22 is increased, the threshold voltage necessary to bridge the spark gap 22 will increase, and the resulting discharge of energy is greater. Conversely, if the distance between the terminals of the spark gap 22 is decreased, the threshold voltage necessary to bridge the spark gap 22 will decrease, and the resulting discharge of energy is reduced. The spark gap 22 may be mechanically adjusted by any simple, well-known mechanical linkage.

The air core resonant transformer 4 is tuned such that the voltage pulse in the variable inductor 24 induces a resonant voltage in the Tesla coil 26. The air core resonant transformer 4 is tuned by adjusting the inductance of the variable inductor 24 until the resonant voltage is produced. The resonance in the circuit amplifies the voltage produced in the Tesla coil 26 which, at its peak, fluctuates between 0 and 750,000 V near the light emitting system 6. The Tesla coil 26 behaves as an antenna in response to the resonant voltage and produces electromagnetic emissions over a broad range of harmonic frequencies.

The resonant voltage in the Tesla coil 26 is applied to the first electrode 34 in each of the tubes 32 in the light emitting system 6. The high voltage passes from the first electrode 34 to the second electrode 32 through the gas in each tube, and the molecules of the gas, which normally exist as pairs of atoms (e.g., $O_2$), split upon the application of the voltage. The gases produce electromagnetic emissions at higher harmonic frequencies when the molecules recombine. The second electrodes 38 in each of the tubes 32 absorb the voltage pulses which are dissipated to the surrounding atmosphere through arcing. The electromagnetic emissions from the tubes 32 include harmonic frequencies in the visible portion of the electromagnetic spectrum, and each gas produces light having a different color. As a result, when the BELS unit 8 is operating each tube 32 produces visible light having a particular color and arcing occurs from the second plate 40.

The resonant electric field generated in the Tesla coil 26 dissipates as a result of the electromagnetic emissions, and is restored by subsequent discharges across the spark gap 22.

The air core resonant transformer 4 and the light emitting system 6 generate electromagnetic emissions at harmonic frequencies between 500 kHz and 3 GHz in response to the voltage pulses in the variable inductor 24. A patient situated proximate to the unit may benefit from the broad range of harmonic frequencies generated by the BELS unit 8.

The apparatus includes a pulse generator circuit 50 for generating periodic voltage pulses. The pulse generator circuit 50 may be one of many well-known circuits. For example, a pulse generator circuit is disclosed in U.S. Pat. No. 5,556,418 to Pappas entitled "Method and Apparatus for Pulsed Magnetic Induction," which is incorporated in its entirety herein by way of reference. The circuit disclosed by Pappas is a plasma circuit in which the plasma is induced to oscillate and to thereby generate periodic voltage pulses. It should be noted that the plasma circuit disclosed by Pappas has an unpredictable variability (i.e., jitter) in the pulse start time due to the variability of plasma breakdown. In an exemplary embodiment, the pulse generator 50 is designed to provide variability of several microseconds in the pulse start time.

In an exemplary embodiment, the pulse generator 50 is connected to a normal 50/60 Hz power circuit and includes a transformer (not shown) to generate high voltage pulses that are coupled to a coil 52 through conductors 54. The coil 52 provides inductive coupling between the pulse generator circuit 50 and the air core resonant transformer 4 of the BELS unit 8. The BELS unit 8 operates in the manner described above, except that it is no longer triggered by the rectified waveform illustrated in FIG. 3. Instead, the air core resonant transformer 4 is triggered by signals generated by the pulse generator circuit 50 and coupled to the air core resonant transformer by the coil 52.

In the embodiment of the apparatus shown in FIG. 1, a first end of the Tesla coil 26 is connected to the light emitting system 6 having one or more translucent gas discharge tubes 32, as previously described with respect to FIG. 2. A second end of the Tesla coil 26 is connected to a ground.

The pulse generator circuit 50 is also connected to a third coil, which is a toroidal coil 64, through flexible conductors 66. The coil 64 is situated in a protective casing 68 having a rigid handle portion 70. The coil 64 is typically designed to generate a powerful electromagnetic field and comprises multiple turns of a heavy gauge wire. For example, the circuit disclosed by Pappas uses 2–10 turns of a heavy gauge conductor. Other alternative designs for the coil 64 may also be used.

The protective casing 68 is sized to be placed on or near localized areas of a patient, and can be manipulated manually with the handle 70. In an exemplary embodiment, the coil 64 is coupled in parallel with the coil 52 and receives the first voltage pulses from the pulse generator circuit 50. The coil 52 and coil 64 may be coupled directly together or isolated by well-known circuitry, which need not be described in greater detail herein. The advantage of coupling the coil 64 and the coil 52 is that the BELS unit 8 operates in synchrony with the pulse generator circuit 50. Under these conditions, the electromagnetic field and visible radiation generated by the BELS unit 8 works in conjunction with the electromagnetic field generated by the coil 64. The patient 48 (see FIG. 2) benefits from the overall exposure of the electromagnetic field generated by the BELS unit 8 operating in conjunction with the localized electromagnetic field generated by the coil 64.

The operation of the apparatus shown in FIG. 1 may now be described. The pulse generator circuit 50 generates the first pulses which are coupled to the coil 52. The coupling between the coil 52 and the air core resonant transformer 4 induces second voltage pulses in the Tesla coil in response to the voltage pulses in the coil 52. The Tesla coil 26 generates a PEMF across a large portion of the radio frequency spectrum in response to the voltage pulses in the coil 52. The primary difference in operation of the Tesla coil 26 in the light emitting system 6 in FIG. 1 compared with the Tesla coil 26 and light emitting system 6 in FIG. 2 is that the Tesla coil 26 in FIG. 1 is triggered in synchronism with the localized electromagnetic field generated by the coil 64 while the circuit in FIG. 2 operates at a pulse rate governed by the power line frequency. It should be noted that the system in FIG. 2 has a pulse rate that is set by the power line frequency and is not controlled by the user. In contrast, the pulse generator circuit 50 of FIG. 1 can generate pulses at a controlled rate. In an exemplary embodiment, the pulse rate of signals from the pulse generator circuit 50 is in the order of one to three pulses per second. In addition, the pulse generator circuit 50 may provide a small degree of variability (i.e., jitter) between the pulses, as previously described.

The operation of the light emitting system 6 shown in FIG. 1 is also similar to the operation of the light emitting system 6 shown in FIG. 2 except that the light emitting system of FIG. 1 is triggered in a controlled manner by the pulse generator circuit 50 at a very low repetition rate. The voltage pulses in the Tesla coil 26 excite the gas molecules in each of the tubes 32 of the light emitting system 6 to fluorescence such that each tube emits a series of pulses having a frequency in the visible portion of the spectrum at a wavelength corresponding to the gas in the tube. The voltage pulses from the Tesla coil 26 travel through the tubes 32 in the light emitting system 6 to the second plate 40, and are discharged by arcing to the surrounding environment from the second plate.

The coil 64, which receives the voltage pulses from the pulse generator circuit 50, generates widely spaced (i.e., low repetition rate), fast rise time, high-current EM pulses in the VHF or UHF spectrum in response to the voltage pulses. The PEMF generated by the Tesla coil 26, the pulsed light emissions from the light emitting system 6 and the PEMF generated by the coil 64 are synchronized because each is induced by the voltage pulses produced by the pulse generator circuit 50. The advantage of such synchronization is that the patient 48 is surrounded by the PEMF generated by the BELS unit 8, the wavelengths of light emitted from the light emitting system 6, and the localized PEMF generated by the coil 64.

The apparatus shown in FIG. 1 is used to treat a patient in the following manner. The patient is situated two to three feet from the Tesla coil 26 such that the patient 48 is substantially surrounded by a low rate PEMF from the Tesla coil and the light emitting system 6. The coil 64 is placed proximate to a selected area of the body that may benefit from a more focused application of PEMF energy. The PEMF generated by the coil 64 is focused on the selected area of the body. Therefore, the patient 48 benefits from the general exposure to the broad band PEMF generated by the Tesla coil 26, the wavelengths emitted by the light emitting system 6, and the broadband PEMF focused by the coil 64.

A patient 48 (see FIG. 2) undergoing treatment with the apparatus shown in FIG. 1 may be placed in the proximity of the apparatus for a selected period of time, and the procedure may be repeated as often as required. Each exposure to the apparatus may be timed according to the needs of the patient 48. The application of the focused PEMF from the coil 64 may also be carried out periodically as necessary in conjunction with the exposure to the synchronized PEMF generated by the Tesla coil 26 and the light emissions from the light emitting system 6.

The system 49 may be used to treat a wide variety of ailments, including fatigue, pain, injury trauma, disease, including cancer, parasitic infections such as HIV, AIDS, malnutrition, and depression. In typical treatment, the patient 48 is seated in proximity with the Tesla coil 26 and the coil 64 is placed in proximity with a selected portion of the patient for a period of time and a frequency sufficient to achieve beneficial effects. For example, the patient may be treated two to three times per day for ten minutes per treatment. The duration and frequency of treatment may be varied to achieve optimal beneficial results for the patient 48.

In another embodiment, a method for the treatment of AIDS and AIDS-related illnesses are disclosed. Human acquired immunodeficiency syndrome or "AIDS" is a fatal disease for which there is presently no cure. The disease is believed to be caused by a virus known as the human immunodeficiency virus, commonly referred to as "HIV." The virus is transmitted by HIV-infected individuals through exchange of bodily fluids. HIV infection results most commonly from sexual contact with an infected partner and the sharing among intravenous drug users of hypodermic syringes previously used by an infected individual. A pregnant HIV-infected mother may infect her unborn child by trans-placented transmission, and HIV-contaminated blood is a possible source of infection for individuals subject to blood transfusion.

HIV infection causes a suppression of the immune system. This immune suppression renders the infected individual vulnerable to a variety of opportunistic infections and conditions that are otherwise kept in balance by a healthy immune system. Fatalities result from HIV infection due to the inability of AIDS patients to respond to treatment of the opportunistic infections and conditions as a consequence of their compromised immune systems. Because the virus can often remain dormant, the manifestation of AIDS from HIV infection may take as long as ten years.

One approach to the treatment of AIDS has targeted the opportunistic infections and conditions which result from HIV infection. While such treatment does not target the underlying HIV infection, it does prolong and enhance the quality of life of the infected individual.

A method according to an embodiment of the present invention provides for the treatment of a patient 48 with AIDS or an AIDS-related illness with the BELS unit 8 alone is illustrated in FIG. 2. The patient 48 may be situated within 2–3 feet of the BELS unit 8 such that the patient receives the full benefit of the dense range of harmonic frequencies between 500 kHz and 3 GHz generated by the BELS unit 8. The patient 48 may be exposed periodically to the BELS unit 8 as necessary for the treatment of the AIDS-related illness. For example, the patient 48 may be exposed to the BELS unit 8 once every two days for a selected period of time each day. The length of each exposure, and the frequency of such exposures may be varied to suit the needs of the patient 48.

In a pilot study, ten patients were treated using the BELS unit 8. Six of the ten patients were diagnosed as HIV positive. The patients ranged from 30 to 72 years of age, with an average age of 44.6 years. The pilot study ran for a period of 10 weeks. Patients were exposed to the electromagnetic fields for five to 20 minutes, three times per week. None of the patients involved in the pilot study were taking any allopathic medications during the study. The pilot study concluded that the BELS unit 8 was effective for treating many of the AIDS-related symptoms, such as chronic fatigue and pain syndrome, thrush, headaches, and blurred vision. Variations in the PCR levels of HIV positive patients was inconclusive. However, the BELS unit 8, used in accordance with the principles of the present invention, has been shown to provide relief from many of the symptoms that accompany AIDS and to increase T-cell count and reduce viral load in some AIDS patients.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An apparatus for generating therapeutic pulsed electromagnetic fields for use on a patient, comprising:

a pulse generator circuit generating first voltage pulses;

a resonant circuit having a first coil coupled to the pulse generator circuit to receive said first voltage pulses, said resonant circuit generating a first pulsing electromagnetic field in response to said first voltage pulses with said first pulsing electromagnetic field being sufficiently large to envelop substantially all of the patient; and a second coil coupled to the pulse generator circuit to receive said first voltage pulses, said second coil generating a second pulsing electromagnetic field in response to said first voltage pulses with said second pulsing electromagnetic field being localized to a selected portion of the patient, said first and second pulsing electromagnetic fields being time-synchronized with each other by said first voltage pulses.

2. The apparatus of claim 1 wherein the pulse generator circuit comprises a plasma discharge circuit.

3. The apparatus of claim 1 wherein said pulse generator comprises first and second electrodes spaced apart from each other at a variable distance, said pulse generator generating a short duration plasma discharge between said first and second electrodes at a predetermined time interval.

4. The apparatus of claim 1 wherein said pulse generator generates said first voltage pulses at predetermined time intervals.

5. The apparatus of claim 1 wherein said pulse generator generates said first voltage pulses at variable time intervals.

6. The apparatus of claim 1, further including a light emitting system including at least a first translucent gas-filled tube, said light emitting system emitting an electromagnetic signal having one or more selected frequencies in response to said first voltage pulses.

7. The apparatus of claim 6 wherein said light emitting system includes a plurality of translucent gas-filled tubes, each translucent gas-filled tube containing a selected gas to emit light at a wavelength corresponding said selected gas.

8. The apparatus of claim 1 for the therapeutic treatment of a patient wherein the patient is positioned in proximity with said resonant circuit so as to be generally subjected to said first pulsing electromagnetic field, said second coil being positionable in proximity with a selected portion of the patient to subject the selected portion of the patient to said second pulsing electromagnetic field.

9. The apparatus of claim 1 wherein said first pulsing electromagnetic field generated is in the radio frequency spectrum.

10. The apparatus of claim 1 wherein said pulse generator is inductively coupled to said resonant circuit by a third coil.

11. The apparatus of claim 1 for the therapeutic treatment of a patient wherein the second coil is sized to be placed proximate to said selected portion of the patient.

12. An apparatus for generating pulsed electromagnetic fields for the therapeutic treatment of a patient, comprising:
a signal generator to generate a first voltage signal;
means for generating a first electromagnetic field in response to the first voltage signal;
means for receiving the first electromagnetic field and in response thereto generating a second electromagnetic field large enough to envelop substantially all of the patient and a second voltage signal;
means for emitting visible light in response to the second voltage signal; and
means, coupled to the signal generator, for generating a localized electromagnetic field in response to the first voltage signal, said localized magnetic field being sized to expose a selected portion of the patient thereto.

13. A method for the therapeutic treatment of diseased cells in a patient in need thereof, the method comprising the steps of:
generating a first series of pulses;
coupling said first series of pulses to a resonant circuit to generate a first pulsed electromagnetic field in response thereto;
coupling said first series of pulses to a first coil to generate a second pulsed electromagnetic field in response thereto, said first and second pulsed electromagnetic fields being time-synchronized by said first series of pulses;
exposing the cells generally to said first pulsed electromagnetic field for a therapeutic period of time; and
exposing a selected portion of the cells to said second pulsed electromagnetic field for the therapeutic period of time.

14. The method of claim 13, further including the step of applying signals to a plurality of translucent gas-filled tubes in time-synchronization with said first series of pulses, each translucent tube containing a selected gas and emitting light having a selected wavelength in response to said applied signals.

15. The method of claim 13 wherein the patient is affected with a condition selected from fatigue, pain, injury trauma, disease, cancer, parasitic infections, HIV, AIDS, malnutrition, and depression.

16. A method for the therapeutic treatment of diseased cells in a patient in need thereof, the method comprising the steps of:
generating a first series of pulses;
coupling said first series of pulses to a resonant circuit to generate a first pulsed electromagnetic field in response thereto;
coupling said first series of pulses to a first coil to generate a second pulsed electromagnetic field in response thereto, said first and second pulsed electromagnetic fields being time-synchronized by said first series of pulses;
exposing the cells generally to said first pulsed electromagnetic field for a therapeutic period of time;
exposing a selected portion of the cells to said second pulsed electromagnetic field for the therapeutic period of time; and
applying signals to a plurality of translucent gas-filled tubes in time-synchronization with said first series of pulses, each translucent tube containing a selected gas and emitting light having a selected wavelength in response to said applied signals.

17. The method of claim 16 wherein the patient is affected with a condition selected from fatigue, pain, injury trauma, disease, cancer, parasitic infections, HIV, AIDS, malnutrition, and depression.

* * * * *